United States Patent [19]

Holden

[11] Patent Number: Plant 7,247

[45] Date of Patent: Jun. 12, 1990

[54] VARIETY OF GERANIUM NAMED MARILYN

[75] Inventor: Douglas Holden, Solvang, Calif.

[73] Assignee: Bodger Seeds, Ltd., El Monte, Calif.

[21] Appl. No.: 344,761

[22] Filed: Apr. 28, 1989

[51] Int. Cl.[5] ..... A01H 5/00

[52] U.S. Cl. ..... Plt./68

[58] Field of Search ..... Plt./68

*Primary Examiner*—James R. Feyrer

*Attorney, Agent, or Firm*—Webb, Burden, Ziesenheim & Webb

[57] ABSTRACT

A new Geranium cultivar is distinguished by its free basal branching, compactness, lateral and cascading growth habit, small flower clusters which are floriferous and of a clear pink color, heat tolerance, and a superior cutting quality.

1 Drawing Sheet

BACKGROUND OF THE INVENTION

The present invention comprises a new and distinct cultivar of Pelargonium known by the varietal name Marilyn (Oglevee Ltd. No. 1313, Bodger No. 6GM 123-3). The new variety was discovered in a selective breeding program by Mr. Douglas Holden who set out to develop hybrid varieties for vegetative propagation. The new variety is a cross between the seed parent Salmon Floral Cascade and the pollen parent Red Elite.

Salmon Floral Cascade is a commercially available vegetatively propagated cutting variety from Australia and which includes strains of *Pelargonium frutetorum* and *Pelargonium peltatum.* Red Elite is a commercially available single flower zonal (*Pelargonium*×*hortorum*) $F_1$ hybrid seed geranium.

The new cultivar was discovered in August of 1986 at Bodger Seeds, Ltd. in El Monte, Calif., was first asexually reproduced by cuttings at Bodger Seeds, Ltd. at El Monte, Calif. and has been repeatedly asexually reproduced by cuttings at Oglevee Ltd. in Connellsville, Pa. It has been found to retain its distinct propagation through successive propagations.

The hybrid has a different color (clear pink) and larger flowers than the nearest comparative variety, Salmon Floral Cascade.

The new cultivar, when grown in a glass greenhouse in Connellsville, Pa., using full light, 60° F. night temperature, 68° F. day temperature, 71° F. vent temperature, and grown in a soilless media with constant fertilizer of 200–250 parts per million nitrogen and potassium, has a response time from a rooted cutting to a flowering plant in a four inch (10 cm) pot of six weeks.

DESCRIPTION OF THE DRAWING

The accompanying drawing illustrates a new cultivar, the color being as true as possible with color illustrations of this type.

DESCRIPTION OF THE NEW PLANT

The following detailed descriptions set forth the characteristics of the new cultivar. The data which define these characteristics were collected from asexual reproductions carried out by Oglevee Ltd. in Connellsville, Pa. The plants were started as rooted cuttings which were potted on Aug. 1, 1988 and flowered on Sept. 15, 1988 and the plant was maintained until Feb. 15, 1989 when the color readings were taken. The plant histories were taken of plants blossomed under full light in a greenhouse and color readings were taken indoors under 200–220 foot candles of cool white fluorescent light. Color references are primarily to the R.H.S. Colour Chart of The Royal Horticultural Society of London.

THE PLANT

Classification:

*Botanical.*—Hybrid species.

Form: Semi-dwarf; compact.

Height: 19–20 cm from the media surface.

Growth: Free basel branching, lateral and cascading growth habit.

Strength: This variety can be used as a hanging basket geranium or as a bedding plant. As a basket geranium the plant fills out.

Foliage: Zoning present, stalked leaf attachment.

Leaves:

*Size.*—4.5–8 cm across.

*Shape.*—Reniform, cordate base.

*Margin.*—Crenate.

*Texture.*—Pubescent; dull (not reflective).

*Color.*—Top: Outer margin and leaf center: Green group 137A; Zone: Greyed-purple group 187A; Bottom: Yellow-green group 137C.

*Ribs and veins.*—Palmate venation; Yellow-green group 146C;

Petioles: 4.5–8 cm in length; Yellow-Green group 146B.

Stem:

*Color.*—Yellow-green group 146C.

*Internodes.* 1.5–3 cm in length.

THE BUD

Shape: Upright; hemispherical cluster.

Size: 1.5–2 cm across.

INFLORESCENCE

Blooming habit: Continuous; upright; very floriferous blooming habit.

Size: 8–8.5 cm across.

Borne: 3–6 cm above foliage; florets on pedicel; pedicel on peduncle.

Florets:

*Form.*—Flat to slightly cupped.

*Color.*—Red group 55B.

*Petals.*—10–14 in number; separate not united; margin entire obovate; smooth; flat to slightly cupped.

*Floret size.*—3–3.5 cm across.

*Texture and appearance.*—Smooth; clear pink to a small amount of white at petal attachment.

Petaloids:

*Quantity.*—3–6.

*Shape.*—Narrow, elongated, twisted.

*Color.*—Red group 55B.

Pedicel: 2–3 cm in length; Yellow-green group 144A with a cast of Red-purple group 74D.

Peduncle: Arises from the node, opposite leaf petiole; 11–13.5 cm in length.

*Color.*—Yellow-green group 146B with a tinge of greyed-purple group 183B.

Disease resistance: None known.

Lasting quality: This variety holds up extremely well indoors as well as outdoors. Outdoors it is very heat tolerant with very little bloom or leaf burn.

REPRODUCTIVE ORGANS

Stamens:

*Anthers.*—2 mm in length.

*Filaments.*—6–8 mm in length; white in color.

*Pollen.*—Golden brown.

Pistils:

*Number.*—1 with either 5 or 6 parted stigma.

*Length.*—7 mm.

*Stigma.*—5–6 parted at maturity; Red-purple color.

*Style.*—4–5 mm; red-purple color.

Ovaries: 3–4 mm in length; 2 mm across; very pubescent, pale green; superior.

Fruit: None noted.

This unique variety adds a new dimension to the Geranium family. The plant exhibits a neat mound habit that may be used in either hanging baskets or the traditional ground bed. The dark zone compliments the medium green foliage creating an eye catching novelty in the garden. Many small flower clusters create a large continuous bouquet of clear pink color. In comparing this new variety with the current Ivy varieties new on the market, one would find it more floriferous; a much fuller growth habit; better heat tolerance; and a much better cutting producer.

I claim:

1. A new and distinct variety of Geranium plant substantially as herein shown and described and characterized by free basal branching, compactness, lateral and cascading growth habit, small flower clusters which are floriferous and of a clear pink color, heat tolerance, and a superior cutting quality when compared with available Ivy Geranium varieties.

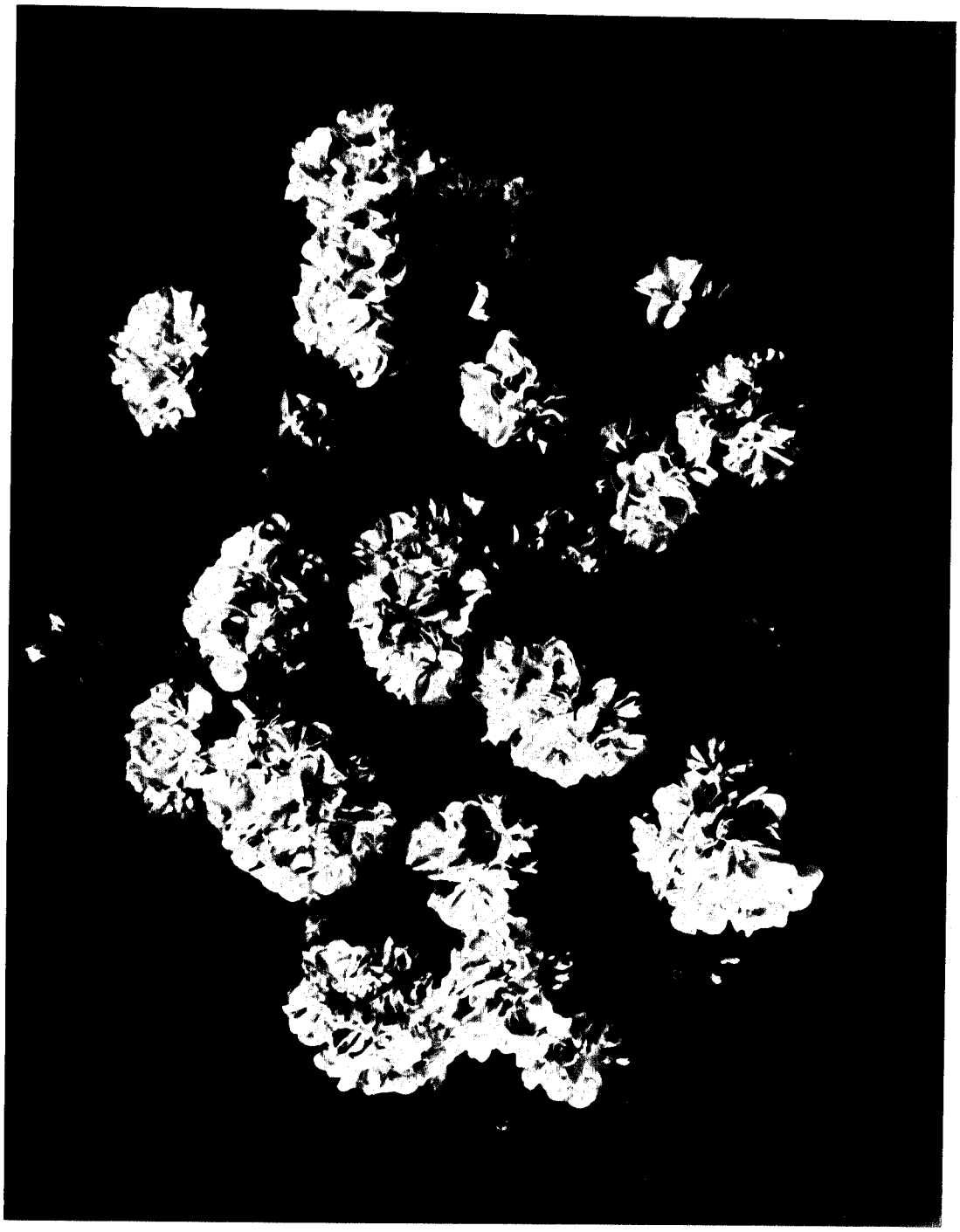

* * * * *